(12) United States Patent
Landry et al.

(10) Patent No.: US 8,753,341 B2
(45) Date of Patent: Jun. 17, 2014

(54) THERMAL BARRIER FOR SUCTION COAGULATOR

(75) Inventors: Dana Landry, Boulder, CO (US); Mark J. Huseman, Broomfield, CO (US); William Robinson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 691 days.

(21) Appl. No.: 12/488,096

(22) Filed: Jun. 19, 2009

(65) Prior Publication Data
US 2010/0324555 A1   Dec. 23, 2010

(51) Int. Cl.
*A61B 18/14*   (2006.01)

(52) U.S. Cl.
USPC ............................................. 606/49; 606/41

(58) Field of Classification Search
USPC .................... 606/27, 35–50; 29/825
See application file for complete search history.

(56) References Cited

U.S. PATENT DOCUMENTS

| | | |
|---|---|---|
| 4,074,718 A | 2/1978 | Morrison, Jr. |
| 5,195,959 A | 3/1993 | Smith |
| 5,312,401 A | 5/1994 | Newton et al. |
| 5,520,685 A | 5/1996 | Wojciechowicz |
| 5,730,742 A | 3/1998 | Wojciechowicz |
| 5,891,141 A | 4/1999 | Rydell |
| 5,895,386 A | 4/1999 | Odell et al. |
| 5,925,045 A | 7/1999 | Reimels et al. |
| 5,972,416 A | 10/1999 | Reimels et al. |
| 6,015,406 A | 1/2000 | Goble et al. |
| 6,027,501 A | 2/2000 | Goble et al. |
| 6,063,079 A | 5/2000 | Hovda et al. |
| 6,074,389 A * | 6/2000 | Levine et al. ................... 606/45 |
| 6,086,585 A | 7/2000 | Hovda et al. |
| 6,379,350 B1 | 4/2002 | Sharkey et al. |
| 6,406,476 B1 | 6/2002 | Kirwan, Jr. |
| 6,464,695 B2 | 10/2002 | Hovda et al. |
| 6,770,070 B1 | 8/2004 | Balbierz |
| 7,879,031 B2 * | 2/2011 | Peterson ......................... 606/41 |
| 2001/0025179 A1 | 9/2001 | Levine |

(Continued)

FOREIGN PATENT DOCUMENTS

| | | |
|---|---|---|
| DE | 2460481 | 12/1974 |
| DE | 2429021 | 1/1976 |

(Continued)

OTHER PUBLICATIONS

European Search Report EP 10166610 dated Sep. 17, 2010.

(Continued)

*Primary Examiner* — Michael Peffley
*Assistant Examiner* — Khadijeh Vahdat

(57) ABSTRACT

An electrosurgical suction coagulator includes a housing having proximal and distal ends and a substantially malleable elongated tube-like shaft extending longitudinally from the distal end of the housing. The elongated tube-like shaft includes a tube-like dielectric sheath and a tube-like electrode disposed coaxially through the tube-like dielectric sheath. The tube-like electrode is configured to operably couple to a source of electrosurgical energy and a proximal end of the tube-like electrode is adapted to operably couple to a source of suction. The tube-like shaft also includes a thermally conductive member. The thermally conductive member is disposed concentrically about the tube-like shaft and at least partially along a longitudinal length of the tube-like shaft. The thermally conductive member is configured to increase a surface area of the tube-like shaft to dissipate thermal energy about the increased surface area.

14 Claims, 4 Drawing Sheets

(56) References Cited

U.S. PATENT DOCUMENTS

| | | | |
|---|---|---|---|
| 2001/0051804 A1* | 12/2001 | Mulier et al. | 606/45 |
| 2002/0049410 A1* | 4/2002 | Noda et al. | 604/113 |
| 2002/0049438 A1 | 4/2002 | Sharkey et al. | |
| 2003/0078576 A1* | 4/2003 | Levine | 606/45 |
| 2003/0181904 A1 | 9/2003 | Levine et al. | |
| 2004/0193150 A1 | 9/2004 | Sharkey et al. | |
| 2006/0235377 A1 | 10/2006 | Earley | |
| 2007/0073285 A1* | 3/2007 | Peterson | 606/41 |
| 2008/0161791 A1 | 7/2008 | Cao et al. | |

FOREIGN PATENT DOCUMENTS

| | | |
|---|---|---|
| DE | 3045996 | 7/1982 |
| DE | 3710489 | 11/1987 |
| DE | 4139029 | 6/1993 |
| DE | 4326037 | 2/1995 |
| DE | 9117019.2 | 4/1995 |
| DE | 19537897 | 3/1997 |
| DE | 9117299 | 4/2000 |
| DE | 19848784 | 5/2000 |
| DE | 29724247 | 8/2000 |
| EP | 0186369 | 7/1986 |
| EP | 0447121 | 9/1991 |
| EP | 0612535 | 8/1994 |
| EP | 0956827 | 11/1999 |
| EP | 1050279 | 8/2000 |
| EP | 1050277 | 11/2000 |
| EP | 1082945 | 3/2001 |
| EP | 1090597 | 4/2001 |
| EP | 1090599 | 4/2001 |
| EP | 1127551 | 8/2001 |
| EP | 1199037 A2 | 4/2002 |
| EP | 1199038 A2 | 4/2002 |
| EP | 1293171 | 3/2003 |
| EP | 1199037 A3 | 7/2003 |
| EP | 1199038 A3 | 7/2003 |
| EP | 1323384 A2 | 7/2003 |
| EP | 1323384 A3 | 1/2004 |
| EP | 1561430 | 8/2005 |
| EP | 1090598 | 9/2005 |
| EP | 1570798 | 9/2005 |
| EP | 1595507 | 11/2005 |
| EP | 1656900 | 5/2006 |
| EP | 1645234 | 12/2006 |
| EP | 1602337 | 12/2007 |
| EP | 2147651 | 1/2010 |
| EP | 2156803 | 2/2010 |
| EP | 2221016 | 8/2010 |
| FR | 1340509 | 9/1963 |
| FR | 2235669 | 1/1975 |
| GB | 1014995 | 12/1965 |
| GB | L014995 | 12/1965 |
| GB | 1222243 | 2/1998 |
| JP | 61-159953 | 7/1986 |
| SU | 1438745 | 11/1988 |
| WO | 91/13593 | 9/1991 |
| WO | 93/03678 | 3/1993 |
| WO | 94/20032 | 9/1994 |
| WO | 96/27337 | 9/1996 |
| WO | 96/39086 | 12/1996 |
| WO | 97/11647 | 4/1997 |
| WO | 98/43264 | 10/1998 |
| WO | 99/15091 | 4/1999 |
| WO | 01/62333 | 8/2001 |
| WO | 01/64122 | 9/2001 |
| WO | 02/47568 | 6/2002 |
| WO | 02/58762 | 8/2002 |
| WO | WO 03061499 | 7/2003 |
| WO | WO 03068095 | 8/2003 |
| WO | 2004/010883 | 2/2004 |
| WO | 2004/045436 | 6/2004 |
| WO | 2004/073753 | 9/2004 |
| WO | 2005/016142 | 2/2005 |
| WO | 2005/060849 | 7/2005 |

OTHER PUBLICATIONS

Grund et al., "Endoscopic Argon Plasma . . . Flexible Endoscopy" Surgery and Allied Technologies, No. 1, vol. 2, pp. 42-46 (Feb. 1994).
Farin et al. "Technology of Argon Plasma . . . Endoscopic Applications" Endoscopic Surgery and Allied Technologies, No. 1, vol. 2, pp. 71-77 (Feb. 1994).
Brand et al. "Electrosurgical Debulking of Ovarian Cancer: A New Technique Using the Argon Beam Coagulator" Gynecologic Oncology 39.
Hernandez et al. "A Controlled Study of the Argon Beam Coagulator for Partial Nephrectomy" The Journal of Urology, vol. 143, May (J.Urol. 143: 1062-1065, 1990).
Ward et al. "A Significant New Contribution to Radical Head and Neck Surgery" Arch Otolaryngol Head Neck Surg., vol. 115, Aug. 1989 pp. 921-923.
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gastrointestinal Bleeding" Advanced Therapeutic Endoscopy, pp. 79-84.
Waye et al., "Techniques in Therapeutic Endoscopy", W.B.Saunders Company, Philadelphia, PA., pp. 1.7-1.15.
European Search Report for 01102843.8-2305 dated May 15, 2001.
International Search Report PCT/US98/19284, dated Jan. 14, 1999.
European Search Report for EP 05002257.3 dated Jun. 1, 2005.
International Search Report for EP 06019572 dated Nov. 21, 2006.
European Search Report EP 07 00 4356 dated Jul. 2, 2007.
European Search Report EP 07 00 4659 dated Mar. 5, 2008.
European Search Report EP 00 12 1241 dated Jan. 17, 2001.
Valleylab in the OR; Tonsillectomy Article; Aug. 2005.
Valleylab Suction Coagulators; May 2009.
International Search Report from PCT-US03-37111 dated Jul. 21, 2004.
International Search Report from PCT-US04-04685 dated Aug. 6, 2004.
International Search Report from EP-0401-5980 dated Sep. 30, 2004.
International Search Report from PCT-US03-22900 dated Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.

* cited by examiner

THERMAL BARRIER FOR SUCTION COAGULATOR

BACKGROUND

1. Technical Field

The present invention relates generally to electrosurgical coagulators and, more particularly, to an electrosurgical suction coagulator having improved thermal insulation between the active electrode and adjacent tissue.

2. Background of Related Art

The coagulation of bleeding blood vessels and tissue using electrically conductive suction tubes is a technique which has been widely used for some time. Typically, a combination electrosurgery and suction device is employed in surgery wherever excessive blood must be removed from the bleeding site in order to facilitate hemostasis of any bleeding vessels.

Electrosurgical suction coagulators which both coagulate blood and desiccate tissue have also been available for some time. Generally, these devices include a shaft formed from a conductive suction tube electrode having an electrically insulating coating over all but a most distal portion of the tube, so that the distal portion forms a generally annular electrode. The shaft may be formed of malleable materials to enable a surgeon to bend the shaft to a desired shape. The distal end can be used as a blunt desiccation device and/or a blunt coagulator. A suction source is attached to a proximal portion of the tube for evacuating excess fluid and debris from the surgical site through the distal end of the tube. The electrode is operably coupled to a source of electrosurgical energy, such as an electrosurgical generator.

The described electrosurgical suction coagulators may have drawbacks. In particular, heat conducted from the suction tube electrode to the outer surface of the shaft may cause the surface of the shaft to reach temperatures of 60° C. or greater. This may be a concern during surgical procedures, such as an electrosurgical adenotonsillectomy, where the shaft of a suction coagulator may be in proximity to, or in contact with, anatomical structures unrelated to the procedure, such as the uvula or the oral commissure. The elevated shaft temperature may have undesirable effects on such unrelated anatomical structures, including uvular edema and erythema of the oral commissure area.

SUMMARY

According to an embodiment of the present disclosure, an electrosurgical suction coagulator includes a housing having proximal and distal ends and a substantially malleable elongated tube-like shaft extending longitudinally from the distal end of the housing. The elongated tube-like shaft includes a tube-like dielectric sheath and a tube-like electrode disposed coaxially through the tube-like dielectric sheath. The tube-like electrode is configured to operably couple to a source of electrosurgical energy and a proximal end of the tube-like electrode is adapted to operably couple to a source of suction. The tube-like shaft also includes a thermally conductive member. The thermally conductive member is disposed concentrically about the tube-like shaft and at least partially along a longitudinal length of the tube-like shaft. The thermally conductive member is configured to increase a surface area of the tube-like shaft to dissipate thermal energy about the increased surface area.

According to another embodiment of the present disclosure, an electrosurgical suction coagulator includes a housing having proximal and distal ends and a substantially malleable elongated tube-like shaft extending longitudinally from the distal end of the housing. The elongated tube-like shaft includes a tube-like dielectric sheath and a tube-like electrode disposed coaxially through the tube-like dielectric sheath. The tube-like electrode is configured to operably couple to a source of electrosurgical energy and a proximal end of the tube-like electrode is adapted to operably couple to a source of suction. The thermally conductive member is made from a material that is less thermally conductive than the tube-like shaft and is disposed concentrically about the tube-like shaft and at least partially along a longitudinal length of the tube-like shaft. The thermally conductive member includes a plurality of raised portions separated from each other by a recessed portion defined therebetween. The thermally conductive member is configured to increase a surface area of the tube-like shaft to dissipate thermal energy about the increased surface area.

The present disclosure also provides a method of manufacturing an electrosurgical tool. The method includes coupling a proximal end of a substantially malleable elongate tube-like shaft to a distal end of a housing. A tube-like dielectric sheath is at least partially disposed on the tube-like shaft. The method also includes coupling a tube-like electrode coaxially through the tube-like dielectric sheath and coupling a proximal end of the tube-like electrode to a source of suction via a lumen to provide fluid communication between the tube-like electrode and the source of suction. The method also includes electrically connecting the tube-like electrode to a source of energy to provide energy to tissue via the exposed distal end of the tube-like electrode and coupling a thermally conductive member to the tube-like shaft to increase a surface area of the tube-like shaft to dissipate thermal energy about the increased surface area.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
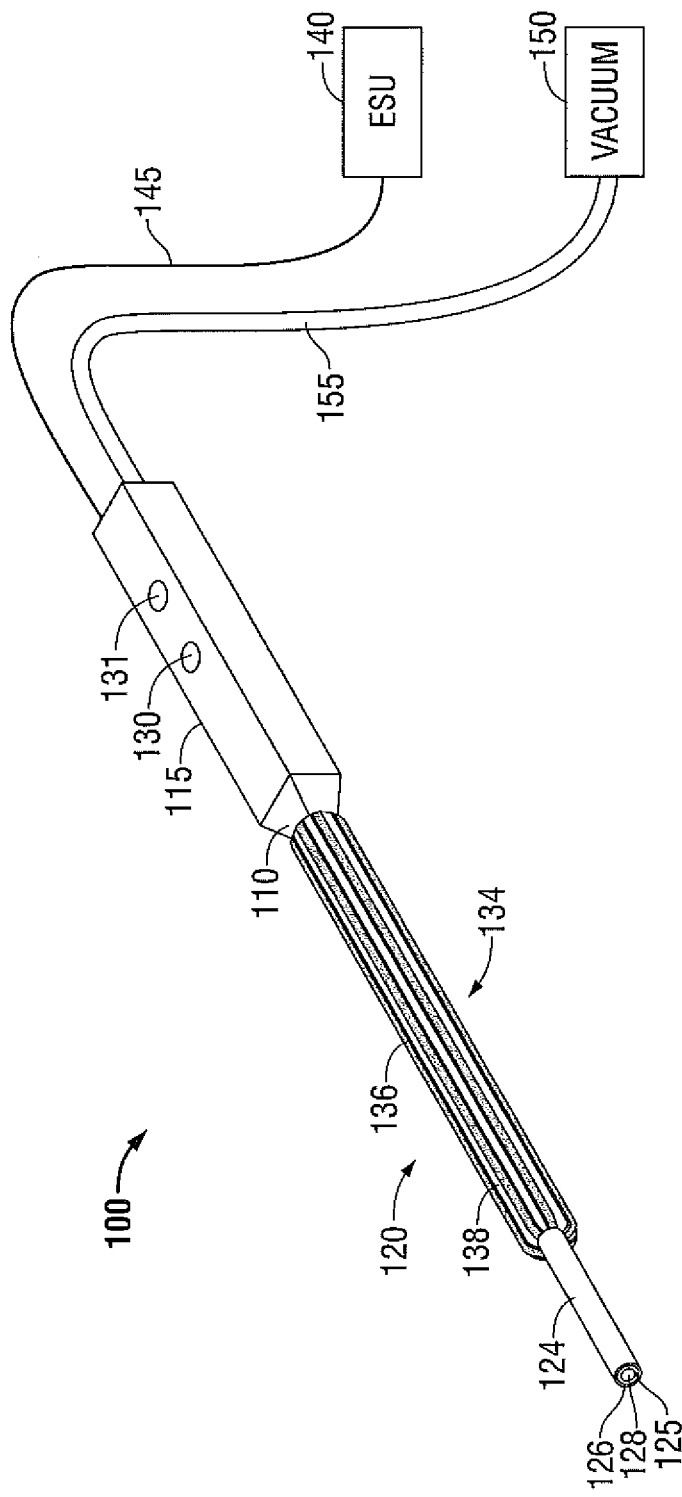
FIG. 1 is an oblique view of an embodiment of an electrosurgical suction coagulator system in accordance with the present disclosure.

Particular embodiments of the present disclosure are described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 2A:
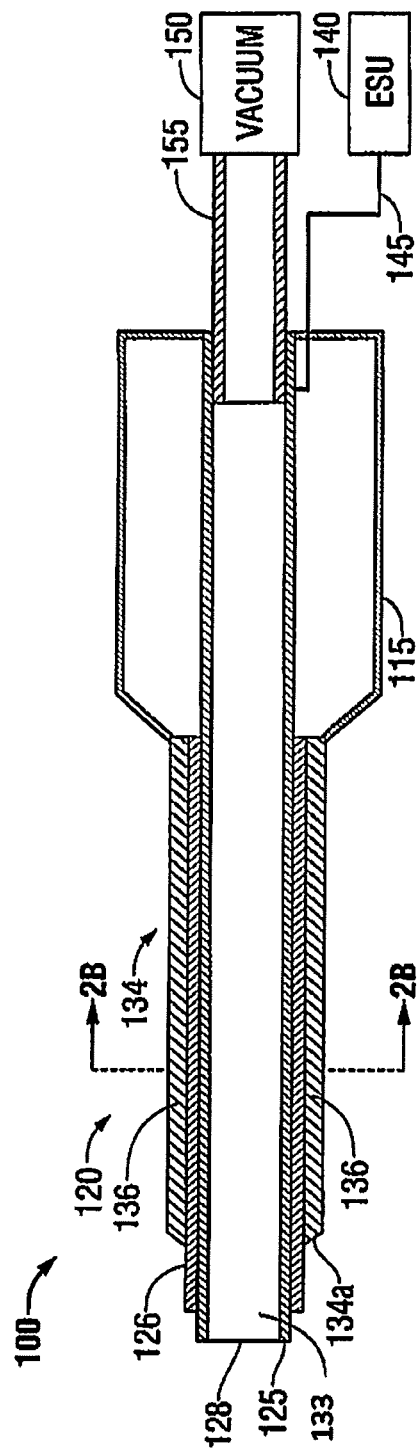
FIG. 2A is a side cutaway view of the electrosurgical suction coagulator of FIG. 1.
Figure 2B:
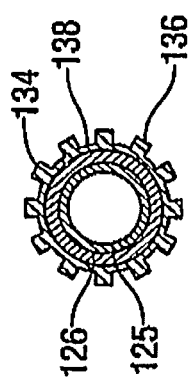
FIG. 2B is a section view of the electrosurgical suction coagulator of FIG. 2A.

With reference to FIGS. 1, 2A, and 2B, an electrosurgical suction coagulator system 100 is presented having a suction coagulator 110 that is operably coupled to an electrosurgical generator 140 via a conductor 145. Suction coagulator 110 is operably coupled to a vacuum source 150 by a lumen 155. Suction coagulator 110 includes a handle 115 disposed at a proximal end thereof and an elongated shaft 120 extending distally from the handle 115. Shaft 120 includes an insulating sheath 126 disposed at least partially thereon. Insulating sheath 126 is formed from any suitable dielectric material, for example, polymeric materials such as PU, PVC, and the like. The shaft 120 may be formed from material having malleable or flexible properties, for example without limitation, metallic material such as aluminum and alloys thereof.

Shaft 120 includes a tube-like electrode 125 configured to deliver electrosurgical energy to tissue. The electrode 125 is disposed coaxially through shaft 120 and is exposed at a distal end 124 of shaft 120 to form an aspiration port 128 defined therethrough. Tube-like electrode 125 defines a conduit 133 longitudinally through shaft 120 to provide suction to a surgical site. By way of conduit 133, aspiration port 128 is in fluid communication with vacuum source 150 via lumen 155. Tube-like electrode 125 may be formed from any suitable electrically conductive material, including without limitation, aluminum or stainless steel. The outer diameter of tube-like electrode 125 is sized similarly to the inner diameter of shaft 120 to form a press-fit or interference-fit between electrode 125 and shaft 120. In use, insulating sheath 126 is configured to provide electrical insulation between electrode 125 and the surface of shaft 120.

A thermally conductive member 134 is disposed concentrically about shaft 120 and extends distally from the handle 115 and terminates at a distal end 134a (see FIG. 2A) that may be tapered. The tapered distal end 134a configuration of member 134 illustrated in FIGS. 1 and 2A is illustrative only in that member 134 may have a blunt distal end. Member 134 is positioned relative to shaft 120 to contact the oral commissure of the patient during a surgical procedure. Thermally conductive member 134 may be overmolded to shaft 120 or, alternatively, the diameter of shaft 120 may be sized similarly to the inner diameter of member 134 to form a press-fit between member 134 and shaft 120 in an extruded manner. Alternatively or additionally, member 134 may be coupled to shaft 120 by any suitable coupling technique such as, for example, crimping, welding, soldering, adhesive, etc. In certain embodiments, member 134 may be electrically insulated utilizing a suitable insulating material (e.g., an insulative coating, a heat-shrink insulator, etc.) at least partially applied thereto.

As best shown in FIGS. 1 and 2B, member 134 includes a plurality of raised portions 136 extending longitudinally along the entire length thereof. Raised portions 136 are separated from each other by a recessed gap 138 defined therebetween and extending longitudinally along the entire length of member 134. Member 134 is formed of a material less thermally conductive than that of shaft 120. For example, member 134 may be formed from, without limitation, a thermoplastic material (e.g., polycarbonate), polyvinyl chloride (PVC), or a surgical grade metal (e.g., stainless steel). In this manner, member 134 operates to impede the proximal propagation of thermal energy along the shaft 120 from the surgical site and/or the distal end 124 thereof during a surgical procedure. Further, the unique geometry configuration of member 134 provides a relatively larger surface area, with respect to the shaft 120 itself, over which thermal energy may migrate and/or dissipate. In this manner, the temperature of the surface area of the suction coagulator 110 that contacts the oral commissure of the patient during a surgical procedure (i.e., member 134) may be reduced. Further, the surface area that comes in contact with the oral commissure of the patient is reduced by virtue of the recessed gaps 138 defined between raised portions 136.

In embodiments, handle 115 includes a control 130 (e.g., handswitch) for controlling the application of electrosurgical energy, i.e., activation and deactivation of an electrosurgical signal. Handle 115 includes an additional or second control 131 for controlling the application of suction to the surgical site. In embodiments, control 131 may be operably coupled to a valve (not shown) that may be disposed within handle 115, shaft 120, vacuum source 150, and/or lumen 155. In other embodiments, control 131 may be operably coupled to a regulator, motor control, or other suitable manner of vacuum control.

In embodiments, member 134 extends distally from the housing 115 to between about 50% and about 75% of the longitudinal length of shaft 120. In other embodiments, member 134 may be disposed along the entire length of shaft 120 (i.e., extending from housing 115 to distal end 124 of shaft 120).

In other embodiments, member 134 may be slidable between positions relative to shaft 120. For example, member 134 may be configured to slide to any number of positions along the longitudinal length of shaft 120 between and including a distal-most position, wherein a distal end of member 134 is substantially aligned with distal end 124 of shaft 120, and a proximal-most position, wherein a proximal end of member 134 engages handle 115. An inner surface of member 134 may include any suitable structure configured to lockably engage an outer surface of shaft 120 such that member 134 releasably locks into any one of the above discussed positions along the longitudinal length of shaft 120. For example, member 134 may include tabs or protrusions (not shown) on an inner surface thereof that are configured to align with and engage grooves (not shown) strategically defined in shaft 120 to releasably lock member 134 into a designated position (e.g., in a snap-fit manner). Sliding member 134 into a designated position may provide a tactile and/or audible response to alert the user that member 134 has been locked into position.

Figure 3:
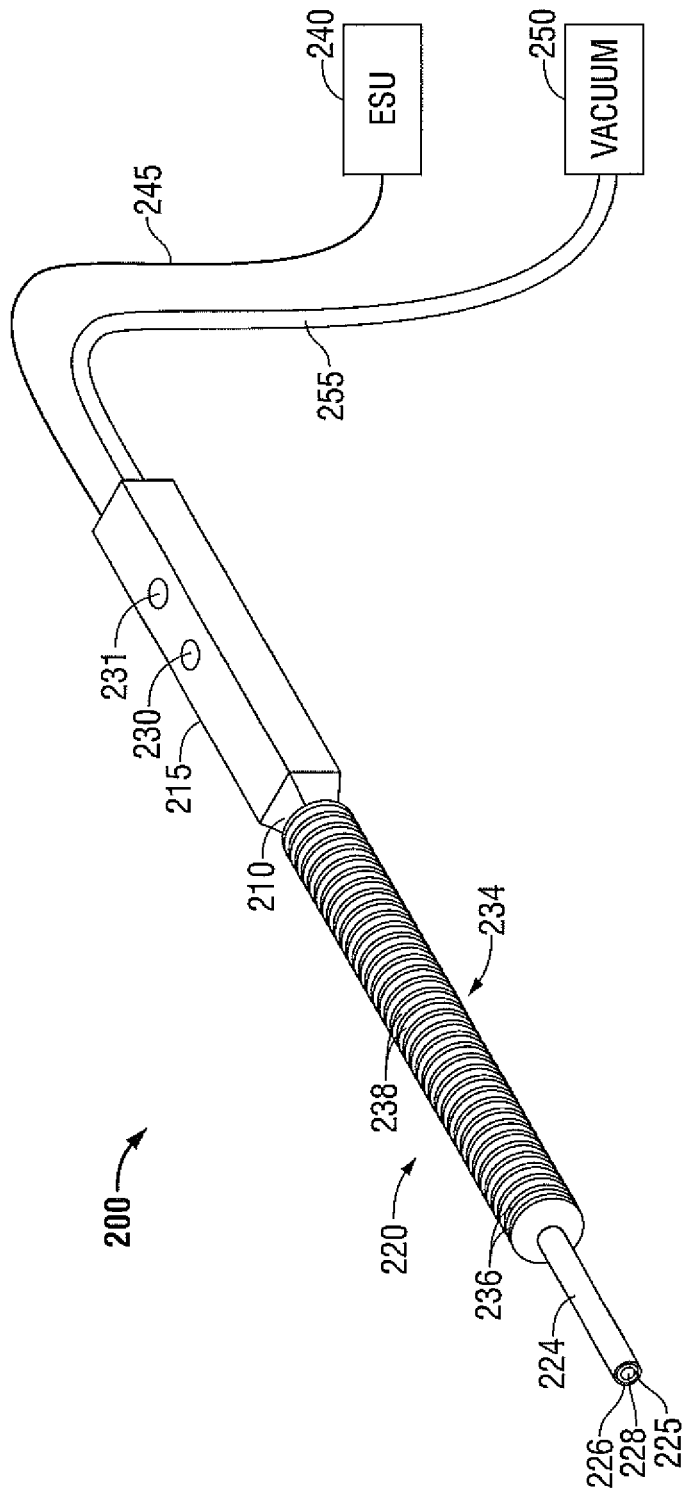
FIG. 3 is an oblique view of an embodiment of an electrosurgical suction coagulator system in accordance with another embodiment of the present disclosure.
Figure 4A:
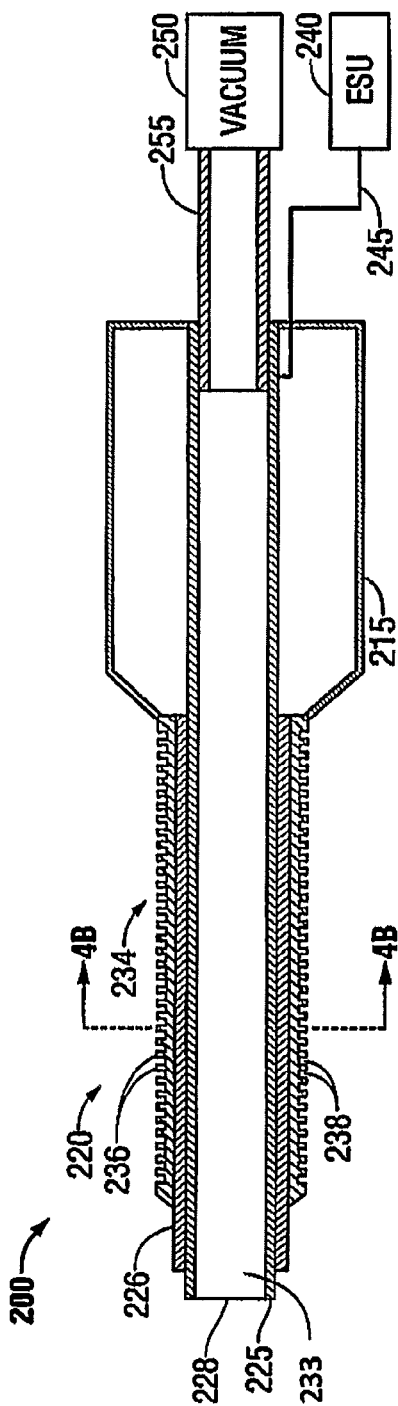
FIG. 4A is a side cutaway view of the electrosurgical suction coagulator of FIG. 3.
Figure 4B:
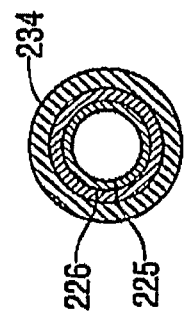
FIG. 4B is a section view of the electrosurgical suction coagulator of FIG. 4A.

Turning now to FIGS. 3, 4A and 4B, a suction coagulator 200 in accordance with another embodiment the present disclosure is operably coupled to an electrosurgical generator 240 via a conductor 245 and includes a housing 215 disposed proximally to an elongated shaft 220. Shaft 220 includes an insulating sheath 226 formed from any suitable dielectric material.

With reference to FIGS. 2, 3A, and 3B, an electrosurgical suction coagulator system 200 is presented having a suction coagulator 210 that is operably coupled to an electrosurgical generator 240 via a conductor 245. Suction coagulator 210 is operably coupled to a vacuum source 250 by a lumen 255. Suction coagulator 210 includes a handle 215 disposed at a proximal end thereof and an elongated shaft 220 extending distally from the handle 215. Handle 215 includes a control 230 (e.g., handswitch) for controlling the application of electrosurgical energy, i.e., activation and deactivation of an electrosurgical signal. Handle 215 includes an additional or second control 231 for controlling the application of suction to the surgical site. Shaft 220 includes an insulating sheath 226 disposed at least partially thereon. Insulating sheath 226 is formed from any suitable dielectric material, for example, polymeric materials such as PU, PVC, and the like. The shaft 220 may be formed from material having malleable or flexible properties, for example without limitation, metallic material such as aluminum and alloys thereof.

Shaft 220 includes a tube-like electrode 225 for delivering electrosurgical energy to tissue. The electrode 225 is disposed coaxially through shaft 220 and is exposed at a distal end 224 of shaft 220 to form an aspiration port 228 defined therethrough. Tube-like electrode 225 defines a conduit 233 longitudinally through shaft 220 to provide suction to a surgical site. By way of conduit 233, aspiration port 228 is in fluid communication with vacuum source 250 via lumen 255. Tube-like electrode 225 may be formed from any suitable electrically conductive material, including without limitation, aluminum or stainless steel. The outer diameter of tube-like electrode 225 is sized similarly to the inner diameter of shaft 220 to form a press-fit or interference-fit between electrode 225 and shaft 220. In use, insulating sheath 226 is configured to provide electrical insulation between electrode 225 and the surface of shaft 220.

A thermally conductive member 234 is disposed concentrically about shaft 220 and extends distally from the handle 215 and terminates at a tapered distal end 234a (See FIG. 3). The tapered distal end configuration of member 234 illustrated in FIGS. 3 and 4A is illustrative only in that member 234 may have a blunt distal end. Member 234 is positioned relative to shaft 220 to contact the oral commissure of the patient during a surgical procedure. Member 234 may be overmolded to shaft 220 or, alternatively, the diameter of shaft 220 may be sized similarly to the inner diameter of member 234 to form a press-fit between member 234 and shaft 220 in an extruded manner. Alternatively or additionally, member 234 may be coupled to shaft 220 by any suitable coupling technique such as, for example, crimping, welding, soldering, adhesive, etc. In certain embodiments, member 234 may be electrically insulated utilizing a suitable insulating material (e.g., an insulative coating, a heat-shrink insulator, etc.) at least partially applied thereto.

As best shown in FIGS. 3 and 4A, member 234 includes a plurality of raised portions 236 disposed circumferentially about member 234 and along the entire length thereof. Raised portions 236 are separated from each other by a recessed gap 238 disposed circumferentially therebetween and along the entire length of member 234. Member 234 is formed of a material less thermally conductive than that of shaft 220. For example, member 234 may be formed from, without limitation, a thermoplastic material (e.g., polycarbonate), polyvinyl chloride (PVC), or a surgical grade metal (e.g., stainless steel). In this manner, member 234 operates to impede the proximal propagation of thermal energy along the shaft 220 from the surgical site and/or the distal end 224 thereof during a surgical procedure. Further, the unique geometry configuration of member 234 provides a relatively larger surface area, with respect to the shaft 220 itself, over which thermal energy may migrate and/or dissipate. In this manner, the temperature of the surface area of the suction coagulator 210 that contacts the oral commissure of the patient (i.e., member 234) during a surgical procedure may be reduced. Further, the surface area that comes in contact with the oral commissure of the patient is reduced by virtue of the recessed gaps 238 disposed between raised portions 236.

The handle 215 of the suction coagulator 210 is substantially as described above with respect to handle 115 of suction coagulator 110 of FIG. 1 and will not be described in further detail herein.

In embodiments, member 234 extends distally from the housing 215 to between about 50% and about 75% of the longitudinal length of shaft 220. In other embodiments, member 234 may be disposed along the entire length of shaft 220 (i.e., extending from housing 215 to distal end 224 of shaft 220).

Thermal conductance, as described herein, may refer to the thermal conductance of the system 100, 200 or, alternatively, to the individual components of the system 100, 200, for example, the thermally conductive member 134, 234, the tube-like electrode 125, 225, and the tube-like shaft 120, 220.

The described embodiments of the present disclosure are intended to be illustrative rather than restrictive, and are not intended to represent every embodiment of the present disclosure. Further variations of the above-disclosed embodiments and other features and functions, or alternatives thereof may be made or desirably combined into many other different systems or applications without departing from the spirit or scope of the disclosure as set forth in the following claims both literally and in equivalents recognized in law.

What is claimed is:

1. An electrosurgical suction coagulator, comprising:
a housing having proximal and distal ends and a substantially malleable elongated tube-like shaft extending longitudinally from the distal end thereof, the elongated tube-like shaft having proximal and distal ends and including:
a tube-like dielectric sheath; and
a tube-like electrode disposed coaxially through the tube-like dielectric sheath and configured to operably couple to a source of electrosurgical energy, the tube-like electrode being adapted at the proximal end thereof to operably couple to a source of suction; and
a thermally conductive member disposed concentrically about the tube-like shaft and extending at least partially along a longitudinal length thereof between the distal end of the housing and the distal end of the tube-like shaft, the thermally conductive member positioned relative to the tube-like shaft such that the entire length of the thermally conductive member is configured to contact a patient and increase a surface area of the tube-like shaft to dissipate thermal energy about the increased surface area, the thermally conductive member including a plurality of raised portions and a plurality of recessed portions, each of the raised and recessed portions disposed longitudinally relative to the tube-like shaft.

2. The electrosurgical suction coagulator according to claim 1, wherein the plurality of recessed portions are configured to decrease a surface area of the tube-like shaft that contacts a patient.

3. The electrosurgical suction coagulator according to claim 1, wherein during activation of an electrosurgical signal a temperature of the thermally conductive member is decreased by the increased surface area of the tube-like shaft.

4. The electrosurgical suction coagulator according to claim 1, wherein a length of the thermally conductive member is between 50% and 75% of the longitudinal length of the tube-like shaft.

5. The electrosurgical suction coagulator according to claim 1, wherein the thermally conductive member is configured to impede the propagation of thermal energy proximally from a distal end of the tube-like shaft.

6. The electrosurgical suction coagulator according to claim 1, wherein the thermally conductive member is made from a material selected from the group consisting of a thermoplastic material, stainless steel, and PVC.

7. The electrosurgical suction coagulator according to claim 1, wherein the thermally conductive member is slidable relative to the tube-like shaft.

8. The electrosurgical suction coagulator according to claim 7, wherein the tube-like electrode defines a conduit adapted to couple to the source of suction to provide fluid communication between the at least one aspiration port and the source of suction.

9. The electrosurgical suction coagulator according to claim 1, wherein the distal end of the tube-like electrode protrudes at least partially from a distal end of the tube-like dielectric sheath.

10. The electrosurgical suction coagulator according to claim 1, wherein the thermally conductive member includes an electrically insulative material applied thereto.

11. The electrosurgical suction coagulator according to claim 1, further comprising at least one control that activates at least one of the source of electrosurgical energy and the source of aspiration suction.

12. The electrosurgical suction coagulator according to claim 1, wherein the tube-like shaft is formed from one of aluminum and aluminum alloy.

13. An electrosurgical suction coagulator, comprising:
   a housing having proximal and distal ends and a substantially malleable elongated tube-like shaft extending longitudinally from the distal end thereof, the elongated tube-like shaft having proximal and distal ends and including:
      a tube-like dielectric sheath; and
      a tube-like electrode disposed coaxially through the tube-like dielectric sheath and configured to operably couple to a source of electrosurgical energy, the tube-like electrode being adapted at the proximal end thereof to operably couple to a source of suction; and
   a thermally conductive member made from a material less thermally conductive than the tube-like shaft and disposed concentrically about the tube-like shaft to extend at least partially along a longitudinal length thereof between the distal end of the housing and the distal end of the tube-like shaft, the thermally conductive member including a plurality of longitudinally disposed raised portions separated from each other by a plurality of longitudinally disposed recessed portions defined therebetween, each of the raised and recessed portions disposed longitudinally relative to the tube-like shaft, the thermally conductive member positioned relative to the tube-like shaft such that the entire length of the thermally conductive member is configured to contact a patient and increase a surface area of the tube-like shaft to dissipate thermal energy about the increased surface area.

14. The electrosurgical suction coagulator according to claim 13, wherein the plurality of recessed portions are configured to decrease a surface area of the tube-like shaft that contacts a patient.

* * * * *